(12) United States Patent
Dou

(10) Patent No.: US 9,700,715 B2
(45) Date of Patent: Jul. 11, 2017

(54) LEAD, DEVICE AND METHOD FOR ELECTRICAL STIMULATION OF DEEP BRAIN

(71) Applicant: Sceneray Co., Ltd, Suzhou (CN)

(72) Inventor: Meijuan Dou, Suzhou (CN)

(73) Assignee: Sceneray Co., Ltd, Suzhou (CN)

( * ) Notice: Subject to any disclaimer, the term of this patent is extended or adjusted under 35 U.S.C. 154(b) by 0 days.

(21) Appl. No.: 14/685,716

(22) Filed: Apr. 14, 2015

(65) Prior Publication Data

US 2016/0089532 A1   Mar. 31, 2016

(30) Foreign Application Priority Data

Sep. 30, 2014   (CN) .................... 2014 2 0571685 U

(51) Int. Cl.
*A61N 1/05* (2006.01)
*A61N 1/36* (2006.01)

(52) U.S. Cl.
CPC ........ *A61N 1/0534* (2013.01); *A61N 1/36082* (2013.01); *A61N 1/36146* (2013.01); *A61N 1/36171* (2013.01); *A61N 1/36185* (2013.01)

(58) Field of Classification Search
CPC ... A61N 1/0529; A61N 1/0534; A61N 1/0531
USPC .................................. 607/116, 45; 600/378
See application file for complete search history.

(56) References Cited

U.S. PATENT DOCUMENTS

| | | | |
|---|---|---|---|
| 2009/0264954 A1* | 10/2009 | Rise | ................... A61N 1/36082 607/45 |
| 2012/0053658 A1* | 3/2012 | Gabriela | .............. A61N 1/0534 607/62 |

FOREIGN PATENT DOCUMENTS

EP   2563463   3/2013

OTHER PUBLICATIONS

Deep brain stimulation in the internal capsule and nucleus accumbens region: responses observed during active and sham programming; J. Neurol Neurosurg Psychiatry 2007; 78:310-314 (published online Sep. 29, 2006); Goodman et al.*
Medtronic DBStm 3387, 3389 Lead kit for deep brain stimulation Implant Manual, 1998.*
Deep brain stimulation of the nucleus accumbens for the treatment of addiction to Kuhn et al. Ann. N.Y. Acada. Sci. 1282 (2013) 119-128 (published Apr. 2013).*

* cited by examiner

*Primary Examiner* — Paula J Stice
(74) *Attorney, Agent, or Firm* — Seed IP Law Group LLP

(57) ABSTRACT

A lead for deep brain stimulation includes a first electrode group and a second electrode group. The first electrode group includes at least one first electrode which is adapted for being positioned in a nucleus accumben of a brain. The second electrode group includes at least one second electrode which is adapted for being positioned in an anterior limb of an internal capsule of the brain. With one single lead implanted in the brain, the first electrode group and the second electrode group simultaneously stimulating the nucleus accumben and the anterior limb of the internal capsule, and the present disclosure improves the effect and safety of DBS in the therapy of drug-addiction, OCD and/or depression.

9 Claims, 4 Drawing Sheets

LEAD, DEVICE AND METHOD FOR ELECTRICAL STIMULATION OF DEEP BRAIN

CROSS REFERENCE TO RELATED APPLICATION

This application claims the benefit of priority to Chinese patent application No. 201420571685.0, titled "LEAD, DEVICE AND METHOD FOR ELECTRICAL STIMULATION OF DEEP BRAIN", filed with the Chinese State Intellectual Property Office on Sep. 30, 2014, the entire disclosure of which is incorporated herein by reference.

BACKGROUND

1. Technical Field

The present disclosure relates to a lead, a device and a method for deep brain stimulation, which belongs to the technical field of implantable medical devices.

2. Description of Related Art

Brain reward circuit, which is composed of a particular part of the midbrain, is involved in mediating the effects of reinforcement. And the midbrain-edge-cortex system reward circuits are relevant to drug-addiction, Obsessive-Compulsive Disorder (OCD) or depression etc.

Drug rehabilitation includes detoxification and relapse prevention. Medically assisted detoxification alone is inefficient as a treatment for addiction, because it is hard to overcome psychological dependence. One effective approach for addiction therapy is the ablation of neurons that play crucial roles in brain reward circuit by surgery. However, this method permanently damages the brain tissues and leads to psychological symptoms, such as loss of memory, personality changes, reduction of sexual desire, or confusion etc.

Deep Brain Stimulation (DBS) system includes an implantable medical device implanted in the body and a lead implanted in the brain. The implantable medical device and the lead are electrical connected. The implantable medical device sends electrical impulses to specific brain nucleus for the treatment of movement and affective disorders. DBS has provided therapeutic benefits for disorders, such as Parkinson's disease, essential tremor, dystonia, chronic pain, major depression and OCD etc. This indicates that DBS can potentially be used in drug rehabilitation to replace the surgical ablation of neurons.

European Patent No. 2563463 discloses a sense electrode combination, which includes one or more electrodes and a physiological model that indicates one or more characteristics of tissue proximate the electrode within a brain of a patient. One or more stimulation electrodes, used to deliver stimulation, may be selected based on a bioelectrical signal sensed in a brain of a patient with a sense electrode combination. The disclosure indicates a combinative stimulation to a brain. However, this combination is conduct through the cooperation of multiple stimulation electrodes.

SUMMARY

The present disclosure provides a lead for deep brain stimulation including a lead body having a proximal section adapted to be electronically coupled to a power source and a distal section having at least two electrode groups. The at least two electrode groups include a first electrode group and a second electrode group. The first electrode group includes at least one first electrode which is adapted for being positioned in a nucleus accumben of a brain. The second electrode group includes at least one second electrode which is adapted for being positioned in an anterior limb of an internal capsule of the brain. The first electrode group and the second electrode group work together to stimulate targets in the brain. In one embodiment of the present disclosure, the first electrode group and the second electrode group simultaneously stimulate the targets in the brain. However, it is understandable to those of ordinary skill in the art that the stimulation method does not limit to the simultaneous stimulation. For example, the first electrode group and the second electrode group can alternately stimulate the targets in the brain which can also achieve the benefit of the present disclosure.

The present disclosure provides a device having the lead described above. The device further includes a control module outside of a brain, a power module electrically connected with the control module and a stimulation output module electrically connected with the control module and the power module.

The present disclosure provides a method for deep brain stimulation including the steps of: S1: implanting the lead into a brain of a patient; and S2: activating the lead to make the first electrode group and the second electrode group work together to stimulate the brain.

The foregoing has outlined rather broadly the features and technical advantages of the present disclosure in order that the detailed description that follows may be better understood. Additional example features and advantages of example embodiments will be described hereinafter.

BRIEF DESCRIPTION OF THE DRAWINGS

The components in the drawing are not necessarily drawn to scale, the emphasis instead being placed upon clearly illustrating the principles of the described embodiments. In the drawings, reference numerals designate corresponding parts throughout various views, and all the views are schematic.

DETAILED DESCRIPTION OF ILLUSTRATED EMBODIMENTS

Figure 1:
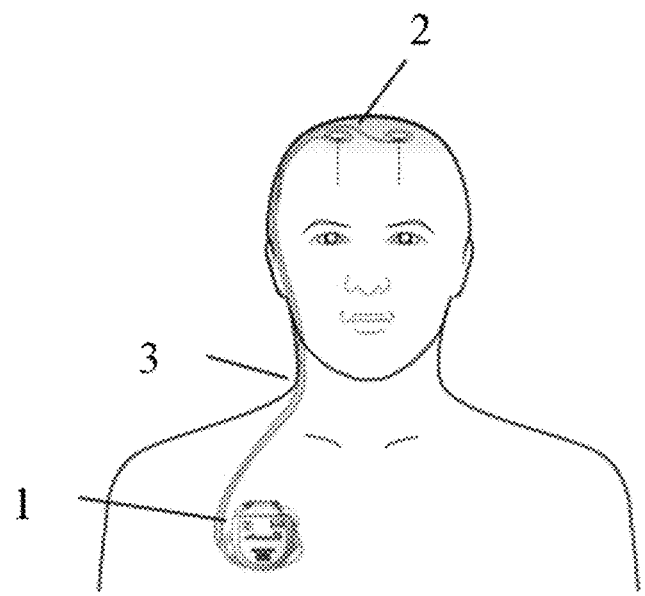
FIG. 1 is a structural schematic view of a DBS device which has been positioned in a human brain.

Reference will now be made to the drawing figures to describe the embodiments of the present disclosure in detail. In the following description, the same drawing reference numerals are used for the same elements in different drawings.

The present disclosure refers to a DBS lead for activating directed electrical stimulation to functional areas in a brain. The said functional areas include nerve nucleuses or nervous tracts with specific functions, which include but not limited to nucleus accumbens and an anterior limb of an internal capsule etc. The present disclosure can be applied for the therapy of psychological disorders, such as drug-addiction, OCD and depression etc. It is also therapeutic benefit for disorders sensitive to the DBS. The present disclosure illustrates a therapy of drug-addiction. However, it is understandable that the present application is not limited to this illustration.

For better understanding, in the present disclosure, positions and directions are defined by the reference of a pulse generator. For example, an end close to the pulse generator is defined as a proximal section, and an end far from the pulse generator is defined as a distal section.

FIG. 1 schematically illustrates an implantable DBS device positioned in a brain. The device includes a pulse generator 1, two leads 2 and an external control device (not shown). The pulse generator 1 is connected with the leads 2 via conductive wires 3 so that the pulse generated by the pulse generator 1 can be transmitted to the leads 2. The pulse signal is transferred from contacts to specific neuron targets in the brain for stimulating the specific neuron targets so as to refresh the function of the human body. Besides, the external control device includes a doctor monitor and a patient controller.

Figure 2:
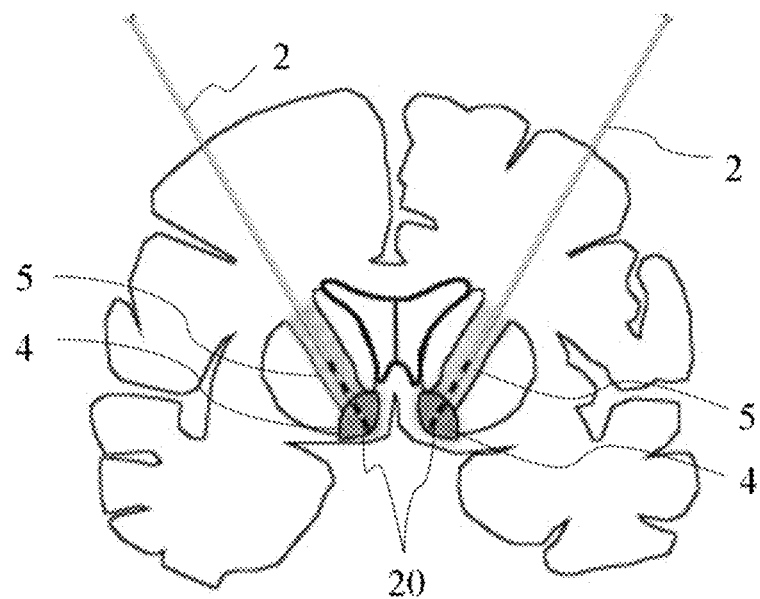
FIG. 2 is a structural schematic view of DBS lead positioned in the brain in accordance with an embodiment of the present disclosure.

FIG. 2 schematically depicts two stimulation leads 2 deeply positioned in the brain. FIG. 2 schematically depicts the leads 2 which are partially embedded simultaneously in the nucleus accumbens 4 and the anterior limbs of the internal capsules 5 at the left side and the right side of the brain. The inventors have discovered that the nucleus accumbens 4 and the anterior limbs of the internal capsules 5 are the two most active stimulation targets in the therapy of drug-addiction. Each nucleus accumben 4 is located adjacent to corresponding anterior limb of the internal capsule 5.

Figure 3:
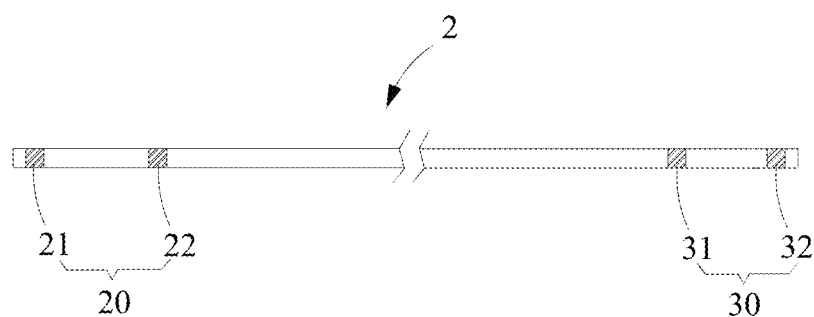
FIG. 3 is a structural schematic view of the DBS lead in accordance with an embodiment of the present disclosure.

FIG. 3 schematically discloses a kind of lead 2 in an embodiment. The lead 2 includes at least two electrode groups 20 in the distal section and at least two contact groups 30 in the proximal section. The two electrode groups 20 include a first electrode 21 and a second electrode 22. Similarly, the two contact groups 30 include a first contact 31 and a second contact 32. In other words, the first and second electrodes 21 and 22 implanted in the brain are corresponding to the distal section of the lead 2 for deep brain stimulation, and the first and second contacts 31, 32 outside of the brain are corresponding to the proximal section of the lead 2 for deep brain stimulation. Concretely, the lead 2 is of a cylinder configuration. Either the electrodes 21, 22 or the contacts 31, 32 is of an annular configuration which surrounds the circumference surface of the lead 2. The electrodes 21, 22 and the contacts 31, 32 are electrically connected with each other, for example via conductive lines. The amount of the contacts 31, 32 is equal to that of the electrodes 21, 22, and each electrode 21, 22 is connected to a corresponding contact 31, 32. The first and the second electrodes 21, 22 are implanted into the target areas of the brain for accurate stimulation. The first and the second contacts 31, 32 are connected to a control module for receiving and transmitting stimulation signals to the first and the second electrodes 21, 22.

In order to accurately cover these two functional areas of the nucleus accumben 4 and the anterior limb of the internal capsule 5, the electrodes 21, 22 need to be well designed so as to adapt the structures of the nucleus accumben 4 and the anterior limb of the internal capsule 5.

Figure 6:
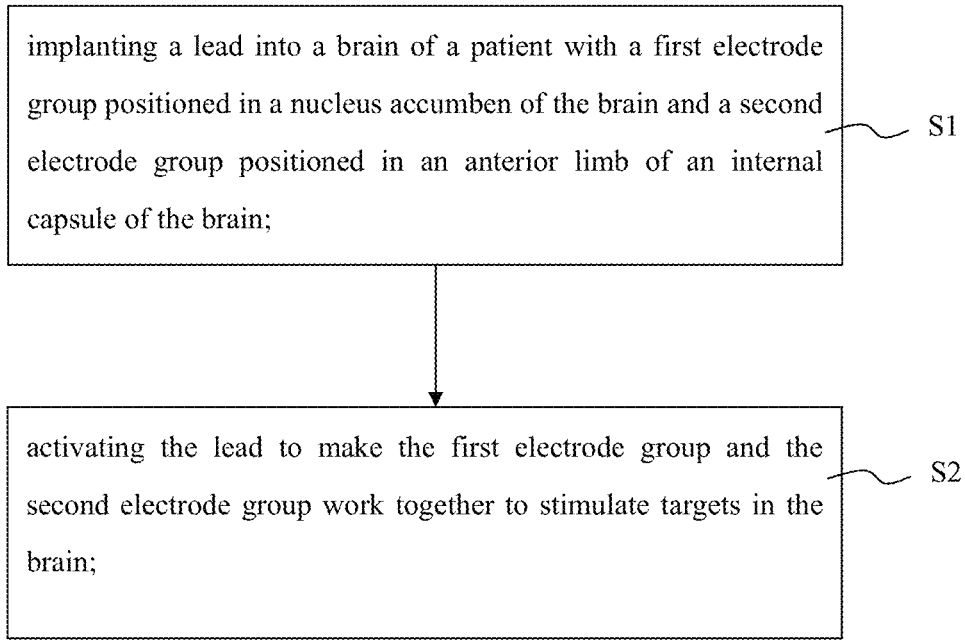
FIG. 6 is a schematic view showing a method for DBS in accordance with an embodiment of the present disclosure.

FIG. 2 and FIG. 6 depict that the first electrode 21 is positioned in the nucleus accumben 4 and the second electrode 22 is positioned in the anterior limb of the internal capsule 5 by surgery. As a result, the two functional areas of the brain are covered by a single lead 2 therein. Latterly, continual electrical stimulation will be applied to jointly stimulate the addicted cells at these two functional areas so as to resist a pathological drug-adhesive nerve center. Each single electrode 21, 22 can be adjusted by the control module via corresponding contact 31, 32. In accordance with the illustrated embodiment of the present disclosure, the control module delivers distinctive stimulation parameters, e.g., pulse amplitude, pulse width or pulse frequency etc., to the nucleus accumben 4 and the anterior limb of the internal capsule 5.

Figure 4:
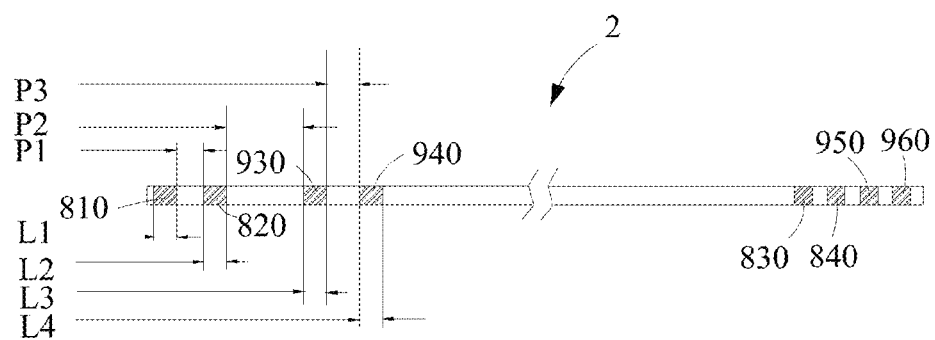
FIG. 4 is a structural schematic view of electrodes and contacts of the DBS lead in accordance with an embodiment of the present disclosure.

Referring to FIG. 4, in another embodiment of the present disclosure, the electrode group 20 include two first electrode 810, 820 disposed along an axis direction of the lead 2 and two second electrode 930, 940 disposed along the axis direction. Accordingly, the contact group 30 includes two first contacts 830, 840 and two second contacts 950, 960. Stimulation frequency of the first electrodes 810, 820 is lower than that of the second electrodes 930, 940. In other words, the pulse frequency applied to the anterior limb of the internal capsule 5 is higher than that to the nucleus accumben 4. Besides, the stimulation parameters can be optimized via continual adaptation.

The first distance between the two first electrodes 810, 820 is P1. The second distance between the two electrode groups 20 is P2. The second distance P2 is larger than the first distance P1. As a result, the first electrodes 810, 820 act on the nucleus accumbens 4, and the second electrodes 930, 940 act on the anterior limbs of the internal capsule 5. Alternatively, the first electrodes 810, 820 can act on a first functional area in the brain, while the second electrodes 930, 940 can act on a second functional area adjacent to the first functional area.

In accordance with an illustrated embodiment of the present disclosure, a third distance between the second electrodes 930, 940 is P3. In an embodiment, the third distance P3 is no less than 0.5 mm. It is understandable that the third distance P3 can be elongated to cover more areas so as to adapt the anterior limb of the internal capsule 5 having large volume.

Temperature rise less than 1° C. in the brain is considered safe. In order to ensure the stimulation intensity as well as limit the temperature rise, each electrode group 20 is preferred to have at least two or more electrodes. In an embodiment, the lead 2 can include three or more electrode groups 20, to stimulate jointly more functional areas of the brain.

Figure 5:
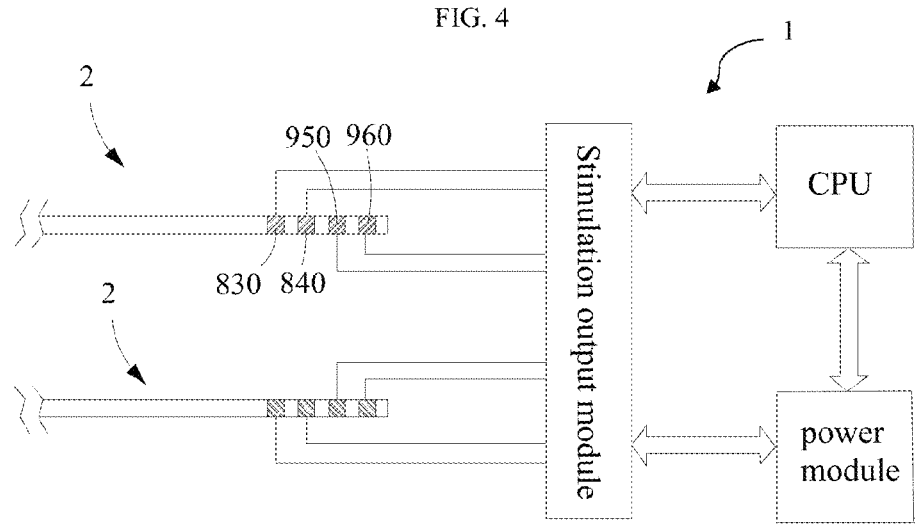
FIG. 5 is a structural schematic view of the DBS device in accordance with an embodiment of the present disclosure.

FIG. 5 schematically depicts implanted components of a DBS device. The implanted pulse generator 1 includes a control module (CPU), a power module electrically connected with the control module and a stimulation output module electrically connected with the control module and the power module. The first and the second contacts 830, 840, 950, 960 of the lead 2 electrically connect with the pulse generator 1 via conductive lines. Each contact 830, 840, 950, 960 independently connects with the pulse generator 1 via a conductive line. The stimulation output module of the pulse generator 1 is capable of outputting parameters, such as pulse width, amplitude and frequency, according to different requirements. As a result, the pulse generator 1 can accurately control each and every contact 830, 840, 950, 960, and can deliver different stimulation parameters to different functional areas in the brain so as to improve therapeutic effect and safety.

In an embodiment, the first distance P1 is no less than 0.5 mm.

In an embodiment, the second distance P2 is larger than 3 mm.

In an embodiment, lengths of the electrodes 810, 820, 930, 940 are L1, L2, L3 and L4 in turn. All these lengths L1 to L4 are no less than 0.5 mm. The lengths of the electrodes 810, 820, 930, 940 could be equal or different.

Three embodiments will be given hereinafter.

First Embodiment

P1=0.5 mm

P2=3.5 mm

P3=0.5 mm

L1=0.5 mm

L2=0.5 mm

L3=0.5 mm

L4=0.5 mm

Second Embodiment

P1=2 mm

P2=4 mm

P3=4 mm

L1=3 mm

L2=3 mm

L3=3 mm

L4=3 mm

Third Embodiment

A representative case: male, 38-yrs old, married; height: 180 cm; weight: 60 kg. This patient has used heroin for 16 years with 0.5 g/day. He felt euphoria when using drugs, but suffered from withdrawal symptoms including irritability, streaming eyes, yawning, muscular soreness and sleeplessness when stopping the drugs. This patient has a strong craving for the drug. The patient has been treated for drug-addiction about ten times. The longest withdrawal history was eighteen months when he worked in other localities, but he relapsed soon after he went back hometown. The longest withdrawal history in the hometown was six months. Before treatment in accordance with an embodiment, the patient had sexual life approximately once per two months and was evaluated as moderate depression.

The present disclosed lead of DBS device was positioned into the patient's brain. 10 days after the implantation, electrical stimulation was provided to the patient with parameters shown in Table 1. Changes in ECoG, local field potential in targeted nuclei, as well as MRI and PET-CT in addiction-relative functional areas were observed after the stimulation. Till writing of this patent application, the patient has no urge for the drug. Four random urine tests for morphine were negative. Three times when got back to the hometown, the patient can still stop craving for the drug. He gained weight of 7 kg, reaching 67 kg. The frequency for sex life rose to two or three times per week. His wife has been pregnant for two months after the patient was treated in accordance with the present disclosure. The evaluation index for the patient's motion, energy and life quality apparently rose after the treatment. No complication was observed during the treatment. By-effects of the electrical stimulation included anaesthesia, mild dizziness, gentle excitement/depression, full/poor energy, which were disappeared after the optimization of the stimulation parameters. By now, the patient has abstained from drugs for 5 months.

TABLE 1

| Functional areas | Amplitude (V) | Pulse width (μm) | Frequency (Hz) |
|---|---|---|---|
| the nucleus accumbens | 2.20 | 240 | 145 |
| the anterior limb of internal capsule | 2.20 | 300 | 185 |

Referring to other cases, the psychological addiction to the drug apparently reduced after the treatment with the disclosure. Indexes for Hamilton Depression Scale (HAMD), symptom checklist (SCL-90), the short form health survey scale, the Obsessive Compulsive Scale (YALE—BROWN) and Wechsler Memory Scale (WMS) were obviously improved compared with pre-operation. There was no significant change in Eysenck Personality Questionnaire (EPQ) before and after the treatment. No complication related to the stereotactic surgery appears. The emotion, spirit, memory and life quality (especially the sexual life) of the patients were improved.

The present disclosure can accurately target at the nuclei, and simultaneously stimulate two neighboring functional areas. Meanwhile, the stimulation parameters of the present disclosure can be optimized to deliver appropriate stimulation to each electrode. By simultaneously stimulating the nucleus accumbens and the anterior limbs of the internal capsules, the present disclosure improves the effect and safety of DBS in the therapy of drug-addiction, OCD and depression, especially in abstain from drugs psychologically.

Moreover, the present disclosure is also capable of delivering pulse to other functional areas so as to disturb the activities of tissues or neurons. With one single lead implanted in the brain, it can cover more extensive functional areas by contrast with current technologies without implanting more leads. The present disclosure can also be applied to the therapy of other disorders relative to the brain, such as paralysis and Parkinson's disease as well as mental diseases. In one embodiment of the present disclosure, the first electrode group and the second electrode group simultaneously stimulate the nucleus accumben and the anterior limb of an internal capsule in the brain. However, it is understandable to those of ordinary skill in the art that the stimulation method does not limit to the simultaneous stimulation. For example, the first electrode group and the second electrode group can alternately stimulate the targets in the brain which can also achieve the benefit of the present disclosure.

FIG. 6 illustrates an embodiment of a method. The method includes an act S1 of implanting a lead into a brain of a patient with a first electrode group positioned in a nucleus accumben of the brain and a second electrode group positioned in an anterior limb of an internal capsule of the brain and an act S2 of activating the lead to make the first electrode group and the second electrode group work together to stimulate targets in the brain.

It is to be understood, however, that even though numerous characteristics and advantages of preferred and exemplary embodiments have been set out in the foregoing description, together with details of the structures and functions of the embodiments, the disclosure is illustrative only; and that changes may be made in detail within the principles of present disclosure to the full extent indicated by the broadest general meaning of the terms in which the appended claims are expressed.

What is claimed is:

1. A lead for deep brain stimulation, comprising:
a lead body having a proximal section adapted to be electronically coupled to a power source and a distal section having at least two electrode groups, the at least two electrode groups comprising:
a first electrode group comprising at least one first electrode which is adapted for being positioned in a nucleus accumben of a brain; and
a second electrode group comprising at least one second electrode which is adapted for being positioned in an anterior limb of an internal capsule of the brain; wherein
the first electrode group and the second electrode group are configured to work together to stimulate said nucleus accumben and anterior limb of an internal capsule in the brain, wherein
the proximal section of the lead body comprises at least two contact groups, the at least two contact groups comprising:
a first contact group comprising at least one first contact which is in one-to-one correspondence with the at least one first electrode, the at least one first contact being electrically connected with the at least one first electrode through a conductive line; and
a second contact group comprising at least one second contact which is in one-to-one correspondence with the at least one second electrode, the at least one second contact being electrically connected with the at least one second electrode through another conductive line;
stimulation parameters of the first electrode group and stimulation parameters of the second electrode group are independently adjustable and applied by the first contact group and the second contact group to the first electrode group and the second electrode group, respectively, so that different stimulation parameters can be outputted to said nucleus accumben and said anterior limb; and
the first electrode group comprises two first electrodes which are separated by a first distance (P1), the first electrode group and the second electrode group are separated by a second distance (P2), and the second distance is larger than the first distance (P2>P1).

2. The lead according to claim 1 wherein a stimulation frequency of the first electrode group is lower than that of the second electrode group.

3. The lead according to claim 1 wherein the second distance is larger than 3 mm.

4. The lead according to claim 1 wherein the first distance is no less than 0.5 mm.

5. The lead according to claim 1 wherein the second electrode group comprises two second electrodes which are separated at a third distance (P3), and the third distance is no less than 0.5 mm.

6. The lead according to claim 1 wherein the lead is used for treating drug addiction.

7. A method for deep brain stimulation comprising steps of:
S1: implanting a lead into a brain of a patient, the lead comprising:
a lead body having a proximal section adapted to be electronically coupled to a power source and a distal section having at least two electrode groups, the at least two electrode groups comprising:
a first electrode group comprising at least one first electrode which is positioned in a nucleus accumben of the brain; and
a second electrode group comprising at least one second electrode which is positioned in an anterior limb of an internal capsule of the brain, wherein
the proximal section of the lead body comprises at least two contact groups, the at least two contact groups comprising:
a first contact group comprising at least one first contact which is in one-to-one correspondence with the at least one first electrode, the at least one first contact being electrically connected with the at least one first electrode through a conductive line; and
a second contact group comprising at least one second contact which is in one-to-one correspondence with the at least one second electrode, the at least one second contact being electrically connected with the at least one second electrode through another conductive line; and
the first electrode group comprises two first electrodes which are separated at a first distance (P1), the first electrode group and the second electrode group are separated at a second distance (P2), and the second distance is larger than the first distance (P2>P1); and
S2: activating the lead to cause the first electrode group and the second electrode group to work together to stimulate said nucleus accumben and anterior limb of an internal capsule in the brain, wherein
stimulation parameters of the first electrode group and stimulation parameters of the second electrode group are independently adjustable and applied by the first contact group and the second contact group to the first electrode group and the second electrode group, respectively, so that different stimulation parameters can be outputted to said nucleus accumben and said anterior limb.

8. The method according to claim 7 wherein stimulation frequency of the first electrode group is lower than that of the second electrode group.

9. The method of claim 7 wherein the method comprises treating drug addiction.

* * * * *